(12) United States Patent
Suzuki et al.

(10) Patent No.: US 7,989,190 B2
(45) Date of Patent: Aug. 2, 2011

(54) COMPOSITION FOR ANALYZING NUCLEIC ACID

(75) Inventors: Shigeya Suzuki, Noda (JP); Yukako Kodama, Noda (JP); Keiko Kurosawa, Noda (JP)

(73) Assignee: Kikkoman Corporation, Noda-shi, Chiba (JP)

( * ) Notice: Subject to any disclaimer, the term of this patent is extended or adjusted under 35 U.S.C. 154(b) by 0 days.

(21) Appl. No.: 12/734,378

(22) PCT Filed: Nov. 19, 2008

(86) PCT No.: PCT/JP2008/070975
§ 371 (c)(1),
(2), (4) Date: Apr. 28, 2010

(87) PCT Pub. No.: WO2009/066673
PCT Pub. Date: May 28, 2009

(65) Prior Publication Data
US 2010/0255480 A1    Oct. 7, 2010

(30) Foreign Application Priority Data

Nov. 20, 2007  (JP) ................. 2007-300113
Feb. 26, 2008  (JP) ................. 2008-043830

(51) Int. Cl.
C12N 9/00    (2006.01)
C12N 9/02    (2006.01)
C07K 1/00    (2006.01)

(52) U.S. Cl. .................. 435/183; 435/189; 530/350

(58) Field of Classification Search .................. None
See application file for complete search history.

(56) References Cited

U.S. PATENT DOCUMENTS

| 6,074,859 A | 6/2000 | Hirokawa et al. |
| 2007/0054283 A1 | 3/2007 | Kishimoto et al. |
| 2007/0166729 A1 | 7/2007 | Kambara et al. |
| 2009/0305353 A1 | 12/2009 | Fujii et al. |

FOREIGN PATENT DOCUMENTS

| JP | 2007-097577 A | 4/2007 |
| WO | WO 96/22376 A1 | 7/1996 |
| WO | WO 98/13523 A1 | 4/1998 |
| WO | WO 02/064830 A2 | 8/2002 |

OTHER PUBLICATIONS

Branchini, B.R. et al, "A Mutagenesis Study of the Putative Luciferin Binding Site Residues of Firefly Luciferase", Biochemistry, (2003), vol. 42, No. 35, pp. 10429-10436.
Moyer, J.D. et al, "Nucleoside Triphosphate Specificity of Firefly Luciferase", Analytical Biochemistry, (1983), vol. 131, pp. 187-189.
Nyren, "Enzymatic Method for Continuous Monitoring of DNA Polymerase Activity", Analytical Biochemistry, (1987), vol. 167, pp. 235-238.
Zhou et al, Quantitative detection of single nucleotide polymorphisms for a pooled sample by a bioluminometric assay coupled with modified primer extension reactions (BAMPER), Nucleic Acids Research, (2001), vol. 29, No. 19, e93 (11 pages).
Arakawa et al, "Detection of cariogenic bacteria genes by a combination of allele-specific polymerase chain reactions and a novel bioluminescent pyrophosphate assay", Analytical Biochemistry, (2004), vol. 333, p. 296-302.
Supplementary European Search Report dated Dec. 20, 2010 for EP 08 851 813.
Steghens, J.P., et al., "Firefly luciferase has two nucleotide binding sites: effect of molecule monophosphate and CoA on the light-emission spectra," *Biochemical Journal*, vol. 336, (1998), pp. 109-113.
Conti, E., et al., "Cyrstal structure of firefly luciferase throws light on a superfamily of adenylate-forming enzymes," Research Article, vol. 4, No. 3, (1996), pp. 287-298.
Ayabe, K., et al., "The role of firefly luciferase C-terminal domain in efficient coupling of adenylation and oxidative steps," *FEBS Letters*, vol. 579, No. 20, (2005), pp. 4389-4394.

*Primary Examiner* — Suzanne Noakes
*Assistant Examiner* — Jae W Lee
(74) *Attorney, Agent, or Firm* — Holtz, Holtz, Goodman & Chick, P.C.

(57) ABSTRACT

The present invention provides a firefly luciferase for inexpensive, highly accurate and highly sensitive nucleic acid analysis that uses dATP instead of an expensive reagent having low reactivity to DNA polymerase in the manner of dATPαS, a method of analyzing nucleic acid that uses that luciferase, and a kit for analyzing nucleic acid thereof.

The present invention relates to a composition for analyzing nucleic acid that contains luciferase for which reactivity to dATP is equal to or less than 1/400 reactivity to ATP, a method of analyzing nucleic acid that comprises the use of that composition, and a kit for analyzing nucleic acid comprising that composition.

3 Claims, 1 Drawing Sheet

COMPOSITION FOR ANALYZING NUCLEIC ACID

This application is the United States national phase application of International Application PCT/JP2008/070975 filed Nov. 19, 2008.

TECHNICAL FIELD

The present invention relates to a composition for analyzing nucleic acid that contains a mutant firefly luciferase, a method of analyzing nucleic acid using thereof, and a kit for analyzing nucleic acid.

BACKGROUND ART

Firefly luciferase is an enzyme that emits light by converting ATP, D-luciferin and oxygen to AMP, oxyluciferin and carbon dioxide.

Currently known examples of nucleic acid analysis methods based on detection of emitted light using firefly luciferase include a pyrosequencing method (see, for example, Non-Patent Document 1), a gene polymorphism (SNPs) analysis method using the BAMPER method (see, for example, Non-Patent Document 2), and a gene detection method using a hybridization method (see, for example, Non-Patent Document 3).

These nucleic acid analysis methods are based on the principle of converting pyrophosphoric acid, which is released when a nucleotide is incorporated by complementary chain synthesis, to ATP using an enzyme such as ATP sulfurylase or pyruvate phosphate dikinase (PPDK), and measuring light emitted by the formed ATP by a luciferin-luciferase reaction.

For example, in the case of a pyrosequencing method, a primer is hybridized with single-strand DNA (sample nucleic acid) serving as a template, and four types of deoxynucleotides (dATP, dGTP, dCTP and dTTP) are added one type at a time to the reaction liquid in sequence to synthesize a complementary chain. When the complementary chain has been synthesized, pyrophosphoric acid is formed as the reaction product. This pyrophosphoric acid is then converted to ATP by ATP sulfurylase, and the formed ATP is measured for luminescence by a luciferin-luciferase reaction. Next, an unreactive nucleotide is removed by a liquid phase method in which an unreactive nucleotide is decomposed by apyrase and the like, or by a solid phase method in which a template DNA is bound to a solid phase and then it is washed with the reaction liquid. The sequence of the sample nucleic acid is then determined by repeating this series of steps while changing the nucleotide.

Although the length of a base sequence able to be determined with the pyrosequencing method is only about 100 bases at a time, this method is attracting attention as a method that enables large-scale nucleic acid analyses to be performed at low cost by analyzing in parallel using a picotiter plate having several million wells per plate.

However, in each of the types of nucleic acid analysis methods based on the principle described above, it is frequently necessary to add a reagent in the form of dATP to the reaction liquid to serve as a substrate of the complementary chain synthesis reaction. Moreover, dATP is also frequently contained in the sample nucleic acid. Since dATP has a structure that resembles that of ATP, although it is much weaker than ATP, it acts as a substrate of luciferase resulting in luminescence. Thus, when analyzing nucleic acid in a reaction liquid containing this dATP using a luciferin-luciferase reaction, the presence of the dATP increases the amount of background light emitted, resulting in the problem of a decrease in analysis sensitivity.

A method that uses a derivative of dATP in the form of deoxyadenosine α-thiotriphosphate (dATPαS) as an alternative to ATP has been reported that prevents emission of background light caused by dATP (see, for example, Patent Document 1). However, dATPαS is extremely expensive in comparison with dATP, and has problems such as poor incorporation efficiency into DNA polymerase reactions and preventing the complementary chain synthesis reaction from proceeding properly.

In addition, in a pyrosequencing method, a method for inhibiting emission of background light attributable to dATP by reducing the rate of content of dATP has also been reported (see, for example, Patent Document 2). However, when the rate of content of dATP of dATP is reduced, the complementary chain synthesis is unable to be fully completed due to a shortage of the required amount of dATP in the case where thymine (T) is continued in the sequence of the template DNA. Thus, the amount of emitted signal light does not correspond to the number of thymine, and since unreacted thymine remains, the reaction is unable to proceed to the next sequence resulting in the problem of being unable to accurately determine the base sequence being analyzed.

Patent Document 1: International Publication WO 98/13523

Patent Document 2: Japanese Laid-Open Patent Publication No. 2007-68450

Non-Patent Document 1: Anal. Biochem., 1987, vol. 167, pp. 235-238

Non-Patent Document 2: Nucleic Acids Res., 2001, vol. 29(19), p. 93

Non-Patent Document 3: Anal. Biochem., 2004, vol. 333, pp. 296-302

DISCLOSURE OF THE INVENTION

Problems to be Solved by the Invention

The present invention provides a firefly luciferase for inexpensive, highly accurate and highly sensitive nucleic acid analysis that uses dATP instead of an expensive reagent having low reactivity to DNA polymerase such as dATPαS, a method of analyzing nucleic acid and a kit for analyzing nucleic acid using thereof.

Means for Solving the Problems

As a result of conducting extensive studies to solve the above problems, the present applicant found that an inexpensive, highly accurate and highly sensitive nucleic acid analysis method that inhibits emission of background light attributable to dATP can be realized by using a firefly luciferase that has low reactivity to dATP, thereby leading to completion of the present invention on the basis thereof. Namely, the present invention relates to the following:

1. a composition for analyzing nucleic acid, comprising a luciferase for which reactivity to dATP is equal to or less than 1/400 reactivity to ATP;
2. the composition for analyzing nucleic acid described in 1 above, wherein the amino acid at position 425 of luciferase is leucine; the amino acid at position 438 is glycine; the amino acid at position 532 is arginine; the amino acid at position 425 is leucine and the amino acid at position 438 is glycine; the amino acid at position 425 is leucine and the amino acid at position 532 is arginine; the amino acid at position 438 is glycine and the amino acid at position 532 is arginine; the amino acid at position 425 is leucine, the amino acid at position 438 is glycine and the amino acid at position 532 is arginine; the amino acid at position 344 is alanine; the amino acid at position 344 is valine; the amino acid at position 344 is isoleucine; or the amino acid at position 344 is alanine, the amino acid at position 425 is leucine and the amino acid at position 438 is glycine;

3. the composition for analyzing nucleic acid described in 1 or 2 above, wherein the luciferase is derived from *Luciola lateralis*;
4. the composition for analyzing nucleic acid described in 1 above, wherein the luciferase is a chimeric luciferase that has an amino acid sequence of positions 1 to 448 of *Luciola cruciata* on the side of N terminal thereof, positions 217, 219 and 239 each being altered to isoleucine (I), and has an amino acid sequence of positions 447 to 450 of *Photinus pyralis* luciferase on the side of C terminal thereof;
5. a method of analyzing nucleic acid comprising the use of the composition described in 1 to 4 above; and,
6. a kit for analyzing nucleic acid comprising the composition described in 1 to 4 above.

Effects Of The Invention

According to the present invention, highly sensitive analyses of nucleic acids can be carried out while suppressing the effects of emission of background light attributable to dATP.

BEST MODE FOR CARRYING OUT THE INVENTION (Luciferase)

Although examples of the origin of the luciferase (EC 1.13.12.7) used in the present invention include members of the Coleoptera family such as *Luciola cruciata, Luciola lateralis* or *Photinus pyralis*, other sources may be used provided the luciferase demonstrates a luminescence reaction that uses ATP as a substrate and has low reactivity to dATP. In addition, luciferase having a sequence that occurs in nature or that having various types of known mutants may also be used. Luciferase containing mutants introduced for purposes other than reactivity to dATP, such as heat resistance, drug resistance, luminous intensity, duration of luminescence or color of luminescence, can also be used. In addition, luciferase containing mutants inserted for other purposes such as heat resistance or drug resistance can also be used.

The luciferase used in the present invention is preferably *Luciola cruciata* luciferase, *Luciola lateralis* luciferase or *Photinus pyralis* luciferase, and more preferably *Luciola lateralis* luciferase.

(Reactivity to dATP)

In the present invention, it is extremely important that the luciferase used in the luminescence reaction has low reactivity to dATP. "Low reactivity to dATP" refers to reactivity to dATP being relatively low with respect to reactivity to ATP, and the degree thereof being equal to or less than a constant value, when the reactions are carried out under identical conditions. In the case of using luciferase having such properties in the method of the present invention, emission of background light attributable to dATP is inhibited, and highly accurate and highly sensitive measurement values can be obtained.

(Measurement of ATP/dATP Ratio)

The ratio of reactivity to ATP to reactivity to dATP (ATP/dATP) can be used, for example, to express the reactivity of luciferase to dATP in the present invention. Luciferase preferable for use in the present invention can be specified by using this ratio as an indicator. However, this ATP/dATP ratio varies according to reaction conditions such as the concentrations of ATP and dATP used during measurement, pH, reaction temperature, reagent composition and measurement apparatus. In addition, these conditions also fluctuate in a complex manner. For example, the maximum wavelength of light emitted may change as a result of changing the pH, reaction temperature, reagent composition and the like. On the other hand, since the sensitivity of the apparatus used to measure luminescence also varies according to wavelength, in such cases, there may be cases in which different results are obtained depending on the measurement apparatus. In consideration of these circumstances, it is necessary to measure ATP/dATP ratio for specifying an enzyme used in the present invention under fixed conditions.

For example, the ATP/dATP ratio for specifying an enzyme used in the present invention can be measured under the conditions described below.

An ATP/dATP ratio measurement reagent containing luciferase (pH 7.5±0.1, 60 mM tricine, 2 mM EDTA, 20 mM magnesium acetate, 0.2 mM dithiothreitol (DTT), 0.4 mM D-luciferin, 0.1% bovine serum albumin (BSA)) is prepared for use as luminescent reagent in order to examine reactivity to dATP and ATP. The luciferase concentration varies according to the specific activity of the luciferase to be measured, and is preferably adjusted to a concentration that is able to be stably measured with a detector such as the Lumitester C-100N (Kikkoman). The measuring range is preferably 0.01 µg/mL to 10 mg/mL.

With respect to ATP measurement, 0.1 mL of $1\times10^{-7}$ M ATP is added to 0.1 mL of the ATP/dATP ratio measurement reagent (containing luciferase) followed by measuring the amount of light emitted immediately after addition with the Lumitester C-100N.

With respect to dATP measurement, 0.1 mL of $1\times10^{-5}$ M dATP is added to 0.1 mL of the ATP/dATP ratio measurement reagent followed by measuring the amount of light emitted immediately after addition with the Lumitester C-100N.

In order to correct the ATP concentration and dATP concentration, the value obtained by multiplying the luminescence during addition of ATP by 100 and dividing that value by the luminescence during dATP addition can be used for the "ATP/dATP ratio." Measurements are preferably carried out at 25±1° C.

The Lumitester C-100N using a photomultiplier tube for the detector, or a measuring instrument of equal performance, is used for the measuring instrument.

In the case of using luciferase for which the ATP/dATP ratio thereof as obtained under the measuring conditions described above is 400 or more, preferably 800 or more, more preferably 2,000 or more and even more preferably 4,000 or more, background emission attributable to dATP can be inhibited, thereby allowing the obtaining of highly accurate and highly sensitive measured values. On the other hand, in the case of using luciferase having an ATP/dATP ratio of less than 400, background emission attributable to dATP has a detrimental effect on measurement, thereby preventing measurements having adequate accuracy and sensitivity.

(Selection of Luciferase Having Low Reactivity to dATP)

Luciferase having low reactivity to dATP can be selected from various known types of luciferase and luciferase newly prepared on the basis of various types of luciferase sequences by using the indicator described above. Examples of luciferase able to be preferably used in the present invention that have been selected in the manner described above include luciferase in which the amino acid at position 425 of luciferase is leucine, the amino acid at position 438 is glycine, the amino acid at position 532 is arginine, the amino acid at position 425 is leucine and the amino acid at position 438 is glycine, the amino acid at position 425 is leucine and the amino acid at position 532 is arginine, the amino acid at position 438 is glycine and the amino acid at position 532 is arginine, the amino acid at position 425 is leucine, the amino acid at position 438 is glycine and the amino acid at position 532 is arginine, the amino acid at position 344 is alanine, the amino acid at position 344 is valine, the amino acid at position 344 is isoleucine, or the amino acid at position 344 is alanine, the amino acid at position 425 is leucine and the amino acid at position 438 is glycine. Furthermore, the amino acid positions described above are based on the amino acid sequence of luciferase derived from *Luciola lateralis* (SEQ ID NO. 1).

In addition, another example of the aforementioned luciferase is chimeric luciferase (LUC-C) having an amino acid sequence of positions 1 to 448 of *Luciola lateralis* on the side of N terminal thereof, positions 217, 219 and 239 each being altered to isoleucine (I), and has an amino acid sequence of positions 447 to 550 of *Photinus pyralis* luciferase on the side of C terminal thereof.

(Preparation of Mutant Luciferase Having Low Reactivity to dATP)

Luciferase having low reactivity to dATP can be newly prepared using various types of known methods for preparing mutant enzymes. An example of a commonly used method for inserting mutations includes, but it not limited to, a method involving amplification of individual vectors by PCR using mutant primers. In addition, a target luciferase can be searched for among mutant luciferases obtained by random mutation. The amino acid sequence of luciferase is known to demonstrate a high degree of homology over the full length thereof among members of the Coleoptera family, and since, with respect to mutations in a certain luciferase gene, similar effects resulting in improvement of properties are known to be frequently obtained by introducing a mutation into corresponding amino acid residues of luciferase derived from different origins, mutations are preferably introduced while referring to information on various species of Coleoptera. Luciferase can also be prepared that has mutations demonstrating additional effects that improve properties in addition to low reactivity to dATP, and these mutant enzymes having high levels of practical usefulness.

Next, a host is transformed with a plasmid containing the resulting mutant luciferase gene. The resulting transformant is cultured and mutant luciferase is purified from the resulting bacterial cells. An example of a host includes, but is not limited to, *Escherichia coli* strain K-12.

(Nucleic Acid Analysis Method)

Analysis of nucleic acid is carried out by combining the reagent, enzyme and each step as previously described. More specifically, analysis can include a combination of the steps indicated below:

(1) a step of adding four types of dNTP corresponding to the bases A, G, T and C, or at least one type of derivatives thereof to a reaction liquid containing a sample nucleic acid followed by carrying out complementary chain synthesis using the sample nucleic acid as a template;

(2) a step of forming ATP from pyrophosphoric acid formed by the complementary chain synthesis; and, (3) a step of carrying out a determination the presence or absence of complementary chain synthesis and a quantification of the synthesized amount are carried out by detecting luminescence generated by a luciferase reaction in which the ATP is used as the reaction substrate.

Although each of the aforementioned steps may be carried out individually, steps (1) and (2), steps (2) and (3), or steps (1) to (3) can also be carried out simultaneously in a single liquid.

Known concentration ranges employed in various known methods can be used for the concentration range of each component in each of the steps described above.

With respect to the concentration of dNTP, in the case of analyzing nucleic acid using a step-wise complementary chain synthesis reaction in the manner of pyrosequencing and the like, since a shortage of dNTP can cause incomplete synthesis resulting in incorrect sequencing, it is necessary to add a sufficient amount thereof. When analyzing genome sequences in particular, sequences consisting of 10 continuous base sequences are frequently present in a DNA sequence. In order to accurately determine such base sequences, it is necessary to add dNTP at 30 times or more, preferably 60 times or more and more preferably 100 times or more the amount of template DNA. This value is an amount equal to 3 times, 6 times or 10 times the amount of dNTP (equal to 10 times the amount of template DNA) required to synthesize 10 bases.

Light emitted by the luciferase reaction may be measured using a known measurement apparatus. For example, a measurement apparatus using a photomultiplier tube for the detection unit in the manner of the Lumitester C-100N, or a measurement apparatus that uses a photodiode, CCD, C-MOS, instant camera or imaging intensifier for the detection unit, can be used.

(Sample Nucleic Acid)

Examples of sample nucleic acids used in the present invention include various types of nucleic acids used in various types of nucleic acid analysis methods, and more specifically DNA and RNA. The sample nucleic acid can be derived from humans, fungi, procaryotes or viruses, can be that amplified by PCR, or can be that synthesized artificially with a DNA synthesizer and the like. Sample nucleic acids containing a human or microbial genome sequence are particularly preferable.

(dNTP)

Although the dNTP used in the present invention is a deoxyribonucleoside triphosphate, examples of which include deoxyadenosine triphosphate (dATP), deoxyguanosine triphosphate (dGTP), deoxythymidine triphosphate (dTTP) and deoxycytidine triphosphate (dCTP), dideoxyribonucleoside triphosphates in the form of ddATP, ddGTP, ddTTP and ddCTP as well as other dNTP derivatives may also be used, and allow the obtaining of pyrophosphoric acid by complementary chain synthesis due to the action of DNA polymerase. In addition, dNTP of high purity, which do not contain other dNTP, ATP causing background emission or pyrophosphoric acid, are used preferably. dNTP for PCR, sequencing, mutation introduction or cDNA synthesis and the like are available commercially, and these dNTP can also be used.

Contaminating pyrophosphoric acid and ATP can be decomposed in advance by adding an enzyme such as pyrophosphatase or apyrase. Decomposition of pyrophosphoric acid and ATP formed by complementary chain synthesis can also be reduced by removing the added enzyme with an ultrafiltration membrane or by deactivating the added enzyme by adding a drug and the like.

(Complementary Chain Synthesis)

Various known methods can be used for the complementary chain synthesis step used in the present invention. For example, the use of a method in which complementary chain synthesis of a single base is carried out using one type of dNTP in the manner of SNPs analysis enables a base of a target portion to be analyzed according to the presence or absence of complementary chain synthesis. In addition, the use of a method in which complementary chain synthesis is carried out in steps by adding one type of dNTP at a time in the manner of pyrosequencing enables a base sequence of a target portion to be analyzed. Nucleic acid sequences can be identified by adding all four types of dNTP and a known primer followed by testing for the presence or absence of a nucleic acid having a specific sequence based on the presence or absence of complementary chain synthesis.

A DNA amplification method such as PCR, LAMP or ICAN can also be used for complementary chain synthesis used in the present invention. An amount of pyrophosphoric acid is formed during the course of carrying out this complementary chain synthesis that is equivalent to the amount of complementary chain synthesis.

(DNA Polymerase)

The DNA polymerase used in the complementary chain synthesis step of the present invention refers to an enzyme that synthesizes a DNA strand having a base sequence complementary to a nucleic acid by using the nucleic acid as a template, and includes DNA-dependent DNA polymerase that replicates DNA by using DNA as a template, and RNA-dependent DNA polymerase (reverse transcriptase) that replicates DNA by using RNA as a template. There are no particular limitations on the DNA polymerase used in the present invention provided it forms pyrophosphoric acid using deoxyribonucleotide as a substrate.

(Formation of ATP Equivalent to Amount of Pyrophosphoric Acid)

Although various known methods can be used to convert pyrophosphoric acid formed in the complementary chain synthesis step as described above to an equivalent of ATP, methods that use an enzyme are particularly preferable. Examples of enzymes used include, but are not limited to, ATP sulfurylase (EC 2.7.7.4) (Anal. Biochem., 1985, vol. 151(2), pp. 504-509), nicotinamide mononucleotide adenyl transferase (EC 2.7.7.1) (Published Japanese Translation No. 2003-509601 of PCT International Publication), and pyruvate orthophosphate kinase (PPDK) (U.S. Pat. No. 5,891,659, Non-Patent Document 3).

(Nucleic Acid Analysis Kit)

A kit for using in the nucleic acid analysis method of the present invention can be prepared by combining the reagent, enzyme and the like described above. The kit can contain, for example, the components indicated below:
1) four types of dNTP, or derivatives thereof, corresponding to the bases A, G, T and C;
2) DNA polymerase;
3) D-luciferin and luciferase having low reactivity to dATP described in claims 1 to 4; and,
4) AMP, phosphoenolpyruvate, pyruvate phosphate dikinase and/or adenosine 5'-phosphosulfate (APS) and ATP sulfurylase.

Although the mixture amounts of each reagent and enzyme in the aforementioned kit can be varied according to the properties of the enzymes used and measurement conditions, the kit can be prepared such that, for example during the reaction, the concentration of dNTP or derivatives thereof is 0.001 to 1 µM, that of DNA polymerase is 1 to 5000 U/mL, that of D-luciferin is 0.001 to 10 mM, that of luciferase is 1 to 5000 GLU/mL, that of AMP is 0.001 to 10 mM, that of phosphoenolpyruvate is 0.001 to 10 mM, that of pyruvate phosphate dikinase is 0.1 to 1000 U/mL, that of APS is 0.1 to 100 µM, and that of ATP sulfurylase is 0.02 to 2 U/mL.

Although the pH when using the kit can be varied according to the properties of the enzyme used and the like, the kit can be prepared such that the pH is, for example, 6.0 to 8.5.

Enzyme deactivating factors or stabilizers such as magnesium salts and other metal salts, BSA or dithiothreitol (DTT) can also be added.

In addition, apyrase or pyrophosphatase can also be added as enzymes that decompose background ATP and pyrophosphoric acid.

The following provides a more detailed explanation of the present invention through experimental examples and examples thereof. However, the technical scope of the present invention is not limited to these examples.

EXAMPLE 1

1. Luciferase Mutant

*Photinus pyralis* luciferase available from Sigma was used for the *Photinus pyralis* luciferase (wild type). In addition, LUC-H (Kikkoman, product code: 61314) refers to a luciferase having improved stability by altering the amino acid at position 217 of *Luciola lateralis* to leucine (L) and that at position 490 to lysine (K), while LUC-T (Kikkoman, product code: 61315) refers to a luciferase having improved stability by altering the amino acid at position 217 of *Luciola cruciata* to isoleucine (I). Moreover, LUC-C (Kikkoman, product code: 61313) refers to luciferase having the amino acid sequence of positions 1 to 448 of *Luciola cruciata* on the side of N-terminal thereof, each of the amino acids at positions 217, 219 and 239 being altered to isoleucine (I), and having the amino acid sequence at positions 447 to 550 of *Photinus pyralis* luciferase on the side of C-terminal thereof.

Preparation of pET16b-BLU-Y

A primer for full-length (SEQ ID NO. 2) was synthesized to amplify a biotinated luciferase structural gene. PCR was carried out using the aforementioned primer and a commercially available M13-M4 primer (Takara) by using plasmid pHLf248 described in Japanese Patent No. 3466765 (furthermore, *E. coli* JM101[pHLf248] is deposited as FERM BP-5081 at the International Patent Organism Depository of the National Institute of Advanced Industrial Science and Technology) as a template, followed by digesting the resulting DNA fragment with NdeI and HindIII and purifying using agarose gel. On the other hand, plasmid vector pET16b (Novagen) was digested with NdeI and HindIII and purified to construct plasmid pET16b-BLU-Y containing the aforementioned DNA fragment. *E. coli* strain JM109 was transformed by introducing the constructed plasmid therein. The plasmid was purified from the resulting transformant followed by confirming the DNA sequence thereof.

Preparation of pET32-LUC-H

Primers for full-length (SEQ ID NO. 3 and 4) were synthesized to amplify a luciferase structural gene. PCR was carried out using the aforementioned primers by using plasmid pHLfLK described in Japanese Patent No. 3749628 (furthermore, *E. coli* JM109[pHLfLK] is deposited as FERM BP-6147 at the International Patent Organism Depository of the National Institute of Advanced Industrial Science and Technology) as a template, followed by inserting the resulting DNA fragment into BluescriptII digested with SmaI. *E. coli* strain JM109 was transformed by introducing this plasmid therein, and the plasmid was extracted from the resulting transformant. The resulting plasmid was digested with BamHI and XhoI followed by purifying the luciferase structural gene using agarose gel. On the other hand, the plasmid vector into which the DNA fragment is to be inserted was prepared by digesting pET32c (Novagen) with NdeI and BamHI followed by purification and insertion of annealed synthetic oligonucleotides (SEQ ID NO. 5 and 6). After transforming E. coli strain JM109 by introducing this plasmid therein, the plasmid was extracted. After confirming the DNA sequence of this plasmid and digesting with BamHI and XhoI, the plasmid was purified using agarose gel to construct plasmid pET32-LUC-H inserted with the aforementioned DNA fragment containing luciferase structural gene. E. coli strain JM109 was then transformed by insertion of the constructed plasma. The plasmid was purified from the resulting transformant followed by confirming the DNA sequence.

Preparation of Mutant Luciferase 344A, 344V and 344I

PRC primers were synthesized that were designed so as to convert the 344th amino acid residue, leucine, to alanine (A), valine (V) and isoleucine (I) in the amino acid sequence of Luciola lateralis luciferase. The primers were designed so as to create an AatII site not found in native luciferase by introducing a silent mutation into sequences F-344V and I in common in order to facilitate selection of candidate strains. The full length was then amplified by PCR using pET16b-BLU-Y as a template. The combinations of primers were as indicated below.

pHLf344A F-344A (SEQ ID NO. 8), R-344A (SEQ ID NO. 9)

pHLf344V F-344V, I in common, R-344V (SEQ ID NO. 10)

pHLf344I F-344V, I in common, R-344I (SEQ ID NO. 11)

The template plasmid was decomposed by digesting with DpnI using the PCR reaction liquid, and the terminals of the PCR products were phosphorylated by treating with kinase. E. coli strain JM109 was then transformed using the PCR reaction liquid following treatment. The plasmid was purified from the resulting strain JM109 transformant followed by confirming the DNA sequence.

Preparation of Mutant Luciferase 425L, 438G and 532R

Primers were designed in the same manner as described above so that the amino acid at position 425 of the amino acid sequence of Luciola lateralis luciferase is leucine (L), the amino acid at position 438 is glycine (G), and the amino acid at position 532 is arginine (R), followed by amino acid substitution. The combinations of primers used were as indicated below.

pHLf425L F-425L (SEQ ID NO. 12), R-425L (SEQ ID NO. 15)

pHLf438G F-438G (SEQ ID NO. 13), R-438G (SEQ ID NO. 16)

pHLf532R F-532R (SEQ ID NO. 14), R-532R (SEQ ID NO. 17)

In addition, combinations of these mutations were also prepared. Mutation 438G was introduced by PCR in the same manner as described above using pHLf425L as a template (pHLf425L+438G). Moreover, mutation 532R was introduced in the same manner as described above using pHLf425L, pHLf438G and pHLf425L+438G as templates to construct pHLf425L+532R, pHLf438G+532R and pHLf425L+532R, respectively.

Preparation of Mutant Luciferase 344A+425L+438G

A DNA fragment obtained by digesting pHLf425L+438G with ApaI was purified using agarose gel. On the other hand, a DNA fragment obtained by digesting pHLf344A with ApaI was similarly purified as a template to prepare plasmid pHLf344A+425L+438G inserted with the aforementioned fragments. The resulting plasmid DNA was introduced into E. coli strain JM109 to transform the microorganisms followed by purifying the plasmid from the resulting transformant and determining the sequence thereof.

Preparation of Mutant Luciferase 440A

A PCR primer was synthesized that was designed so as to convert the 440th amino acid residue, leucine, to alanine (A) in the amino acid sequence of Luciola lateralis luciferase. The full length was then amplified by PCR using pET32-LUC-H as a template. The combination of primers was as indicated below.

pHLf440A F-440A (SEQ ID NO. 18), R-440A (SEQ ID NO. 19)

The template plasmid was decomposed by digesting with DpnI using the PCR reaction liquid, and introduced into E. coli strain KRX using the PCR reaction liquid after deactivating DpnI by incubating for 20 minutes at 80° C. to transform the microorganisms. The plasmid was purified from the resulting KRX strain transformant followed by confirming the DNA sequence.

Purification of Mutant Luciferases

Mutant luciferases His-LUC-H, 344A, 344V, 344I, 425L, 438G, 532R, 425L+438G, 425L+532R, 438G+532R, 425L+438G+532R, 344A+425L+438G and 440A were prepared by using transformants in which the previously prepared plasmids pET32-LUC-H, pHLf344A, pHLf344V, pHLf344I, pHLf425I, pHLf438G, pHLf532R, pHLf425L+438G, pHLf425L+532R, pHLf438G+532R, pHLf425L+438G+532R, pHLf344A+425L+438G and pHLf440A had been inserted into E. coli strain BL21(DE3) or E. coli strain KRX. Transformants in which plasmids containing each of the mutant luciferase genes had been introduced were inoculated into 2 mL of LB medium containing ampicillin at 50 µg/mL and cultured aerobically at 37° C. Culturing conditions consisted of culturing for 3 hours at 37° C. and rotating speed of 120 rpm, adding IPTG to a final concentration of 1 mM, and then inducing expression for 4 hours at 30° C.

The gathered microorganisms were washed with physiological saline and then suspended in 50 mM sodium phosphate buffer (pH 7.5) followed by ultrasonic homogenization and removal of cellular residue by centrifugal separation.

The resulting centrifuged supernatant was purified using a His-tag purification kit (MagExtractor-His-tag, Toyobo) in accordance with the kit protocol, and then used in the following experiments.

2. Reagents

Reagents were prepared by adding and dissolving the following substances to each of the concentrations followed by use in the following experiments.

(1) ATP/dATP Ratio Measurement Reagent (pH 7.5)
60 mM tricine
2 mM EDTA
20 mM magnesium acetate
0.2 mM dithiothreitol (DTT)
0.4 mM D-luciferin
0.1% bovine serum albumin (BSA)
1 µg/mL luciferase (2) Complementary Chain Synthesis Confirmation Luminescent Reagent
60 mM tricine (Dojindo Laboratories)
2 mM EDTA (Dojindo Laboratories)
20 mM magnesium acetate (Wako Pure Chemical Industries)

0.2 mM DTT (Wako Pure Chemical Industries)
33.8 U/mL PPDK (Kikkoman)
658.8 GLU/mL luciferase
1.8 U/mL apyrase (Sigma)
0.4 mM D-luciferin (YMC)
0.08 mM trisodium phosphoenolpyruvate (Sigma)
0.4 mM AMP (Oriental Yeast)
0.1% BSA (Sigma)
(3) ATP Solution
   $1 \times 10^{-7}$ M ATP (Oriental Yeast)
(4) dATP Solution
   $1 \times 10^{-5}$ M dATP (GE Healthcare Life Sciences)
   3. Measurement of Reactivity to ATP and dATP ATP/dATP ratio measurement reagents were prepared containing each type of luciferase. In the case of ATP measurement, 0.1 mL of $1 \times 10^{-7}$ M ATP was added to 0.1 mL of ATP/dATP ratio measurement reagent followed by measurement of luminescence with the Lumitester C-100N immediately after addition. In the case of dATP measurement, 0.1 mL of $1 \times 10^{-5}$ M dATP was added to 0.1 mL of ATP/dATP ratio measurement reagent followed by measurement of luminescence with the Lumitester C-100N immediately after addition. Values obtained by multiplying the luminescence during addition of ATP by 100 and dividing that value by the luminescence during addition of dATP are indicated as the values for the ATP/dATP ratio. Measurements were carried out at 25° C. The results are shown below.

| Luciferase | ATP/dATP ratio |
| --- | --- |
| *Photinus pyralis* luciferase (wild type) | 100 |
| LUC-H | 160 |
| His-LUC-H | 170 |
| LUC-T | 250 |
| LUC-C | 430 |
| 425L | 500 |
| 438G | 520 |
| 532R | 400 |
| 425L + 438G | 690 |
| 425L + 532R | 590 |
| 438G + 532R | 640 |
| 425L + 438G + 532R | 1,300 |
| 344V | 460 |
| 344I | 720 |
| 344A | 7,200 |
| 344A + 425L + 438G | 16,000 |
| 440A | 240 |

The ATP/dATP ratio for *Photinus pyralis* luciferase (wild type) was 100, that for LUC-T was 250, and that for LUC-H was 160. In addition, the ATP/dATP ratio for His-LUC-H, in which a histidine tag was inserted into LUC-H, was nearly the same as that of LUC-H at 170, thus clearly demonstrating that the insertion of a histidine tag does not have an effect on ATP/dATP ratio.

In contrast, the ATP/dATP ratio for LUC-C was 430, that for 425L was 500 and that for 532R was 400. Continuing, the ATP/dATP ratio for 438G was 520, that for 425L+532G was 590, that for 425L+532R was 640 and that for 425L+438G+532R was 1,300. Moreover, the ATP/dATP ratio for 344A was 7,200, that for 344V was 460, that for 344I was 720, that for 344A+425L+438G was 16,000, and that for 440A was 240.

Although LUC-C is known to be a luciferase that has superior stability in terms of heat resistance and the like as well as high catalytic efficiency (Patent Document: Japanese Patent Application No. H10-548594), there are no reports examining its reactivity to dATP, and was found for the first time here to be an enzyme that has low reactivity to dATP.

344A is a luciferase in which leucine at position 344 of *Luciola lateralis* (equivalent to position 342 in *Photinus pyralis*) has been altered to arginine. According to a report by Branchini et al. using an enzyme similar to this enzyme, although peak luminescence decreased as a result of altering leucine at position 342 of *Photinus pyralis* to alanine, the luminescence pattern clearly demonstrated a longer half-life (Biochemistry, 2003, vol. 42, p. 10429). However, there are no reports examining its reactivity to dATP, and it was found for the first time here that this enzyme has low reactivity to dATP.

Although mutant luciferases containing 425L, 438G, 532R, 440A or combinations thereof have been reported to be mutations that result in increased luminous intensity (Patent Document: Japanese Unexamined Patent Publication No. 2007-97577), the reactivity to dATP of these enzymes has also yet to be investigated, and it was found for the first time here that these enzymes have low reactivity to dATP.

In the case of 425L+438G, which combines the mutations of 425L (ATP/dATP ratio: 500) and 438G (ATP/dATP ratio: 520), the ATP/dATP ratio was 690, while that in the case of 425L+532R, which combines the mutations of 425L and 532R (ATP/dATP ratio: 400) was 590, and that for 438G+532R was 640. In addition, the ATP/dATP ratio for the combination of three mutations in the form of 425L+438G+532R was 1,300. Moreover, since the ATP/dATP ratio for 344A+425L+438G, which combines the three mutations of 344A (ATP/dATP ratio: 7,200), 425L and 438G, was 16,000, it was clearly demonstrated that mutants having even lower reactivity to dATP can be obtained by combining mutations that are effective for lowering reactivity to dATP.

Namely, although reactivity to dATP is lower in comparison with that before mutation in the manner of 440A (ATP/dATP ratio: 240), even in the case of mutations for which that effect is thought to be small when used alone, the effect is thought to be enhanced by combining with other luciferases having a similar effect.

(Nucleic Acid Analysis Using Luciferase of Present Invention)

Nucleic acid analysis was carried out according to the pyrosequencing method by measuring pyrophosphoric acid using PPDK. Although a detailed explanation of the present invention is provided through examples thereof, the examples do not limit the present invention in any way.

Complementary chain synthesis confirmation luminescence reagents were prepared using LUC-H, LUC-T, LUC-C, mutation 425L+438G, mutation 344A and mutation 344A+425L+438G. 0.002 mL of $5 \times 10^{-6}$ M analytical template DNA (SEQ ID NO. 20) (final concentration: $5 \times 10^{-8}$ M) and 0.002 mL of $5 \times 10^{-6}$ M analytical primer DNA (SEQ ID NO. 21) (final concentration: $5 \times 10^{-8}$ M) were added to 0.100 mL of complementary chain synthesis confirmation luminescent reagent followed by the addition of 0.002 mL of 5000 U/mL Exo-Klenow Fragment (Cloned) (Ambion, final concentration: 50 U/mL), bringing to a final volume of 0.2 mL by addition of ultrapure water and heating at 37° C. Measurements were performed for 60 seconds at 1 second intervals by adding 0.03 mL of $1 \times 10^{-5}$ M dCTP or dATP (containing 0.1 U/mL pyrophosphatase) and measuring changes in luminescence over time with the Lumat LB9507 (Berthold).

dATP or dCTP were added to an amount equal to 30 times the amount of the analytical template DNA and analytical primer DNA.

The analytical template DNA and analytical primer DNA contain sequences that emit light by single-base complementary chain synthesis following addition of dCTP but do not demonstrate complementary chain synthesis with other nucleotides.

Changes in luminescence over time were measured when single-base complementary chain synthesis was carried out using each type of luciferase. In the case of LUC-H (ATP/dATP ratio: 160), luminescence at 6 seconds after demonstrating the maximum value in the case of dCTP was about 120% in the case of having added dATP at 30 times the amount of template DNA. Similarly, luminescence in the case of LUC-T (ATP/dATP ratio: 250) was 89%, thus indicating that background emission attributable to dATP cannot be easily distinguished from luminescence attributable to complementary chain synthesis.

However, since luminescence after addition of dATP in the case of LUC-C (ATP/dATP ratio: 430) was 43%, while that in the case of 425L+438G (ATP/dATP ratio: 690) was less than 50% at only 38%, background emission attributable to dATP can be easily distinguished from luminescence attributable to complementary chain synthesis.

Luminescence during addition of dATP decreased as the ATP/dATP ratio of the luciferase used became larger, and hardly any luminescence was observed in the case of 344A (ATP/dATP ratio: 7,200) and 344A+425L+438G (ATP/dATP ratio: 16,000).

Figure 1:
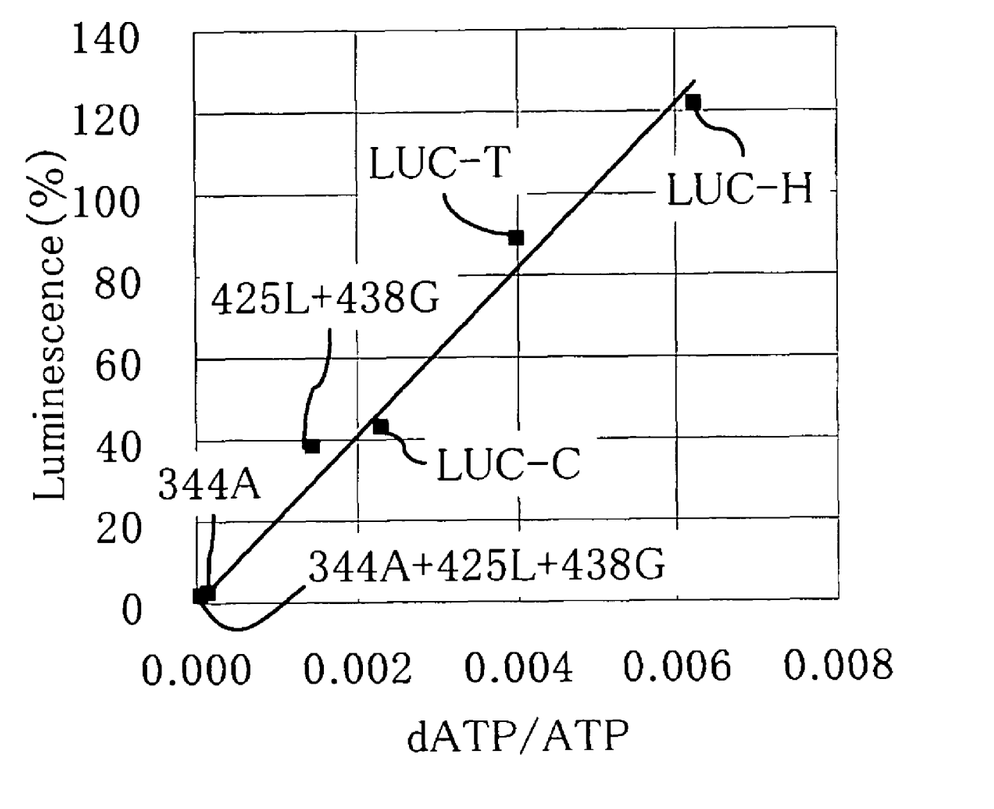
[FIG. 1] indicates the relationship between dATP/ATP ratio and luminescence during addition of dATP in a complementary chain synthesis test.

The relationship between the inverse of the ATP/dATP ratio of each type of luciferase, namely dATP/ATP ratio, and luminescence during addition of dATP in a complementary chain synthesis test is illustrated in FIG. 1. In looking at FIG. 1, a proportional relationship existed between dATP/ATP ratio and luminescence after addition of dATP, and the slope of an approximated straight line was 20,000.

In order to clearly distinguish between luminescence attributable to complementary chain synthesis and luminescence attributable to dATP, it is necessary for the ratio of luminescence attributable to dATP to luminescence during complementary chain synthesis in terms of peak luminescence to be about 50% or less and preferably about 10% or less.

In addition, in consideration of the high frequency of occurrence in genome sequences of identical base sequences continuing for about 10 bases, in order to accurately determine a base sequence without causing a shortage of dNTP, it is necessary to add dNTP in an amount equal to roughly 30 times, preferably 60 times, and more preferably 100 times the amount of the template DNA.

Based on the results of FIG. 1, it can be seen that, in the case the amount of dATP added is 30 times the amount of template nucleic acid, it is necessary to use luciferase having an ATP/dATP ratio of 400 or more in order to reduce background emission attributable to dATP to 50% or less, and use luciferase having an ATP/dATP ratio of 2,000 or more in order to reduce background emission attributable to dATP to 10% or less.

In addition, since a proportional relationship exists between the amount of dATP added and the level of background emission attributable thereto, in the case the amount of dATP added is 60 times the amount of template DNA, it is necessary to use luciferase having an ATP/dATP ratio of 800 or more and 4,000 or more in order to reduce background emission to 50% or less and 10% or less, respectively, while in the case the amount of dATP added is 100 times the amount of template DNA, it is necessary to use luciferase having an ATP/dATP ratio of 1,300 or more and 6,700 or more in order to reduce background emission to 50% or less and 10% or less, respectively.

Although there have been previous reports of the use of luciferase having an ATP/dATP ratio of 400 or less in the manner of *Photinus pyralis* luciferase and LUC-H, there have been no reports of base sequence analyses using luciferase having an ATP/dATP ratio of 400 or more.

The inventors of the present invention found that background emission attributable to dATP can be held to a low level by using luciferase having low reactivity to dATP, and that inexpensive yet highly accurate nucleic acid analyses can be carried out even when using dATP enabling stable complementary chain synthesis.

INDUSTRIAL APPLICABILITY

According to the present invention, inhibiting the effects of background emission attributable to dATP makes it possible to carry out inexpensive, highly accurate and highly sensitive nucleic acid analysis without having to use expensive reagents in the manner of dATPαS.

SEQUENCE LISTING

```
<160> NUMBER OF SEQ ID NOS: 21

<210> SEQ ID NO 1
<211> LENGTH: 548
<212> TYPE: PRT
<213> ORGANISM: Luciola lateralis

<400> SEQUENCE: 1

Met Glu Asn Met Glu Asn Asp Glu Asn Ile Val Tyr Gly Pro Glu Pro
1               5                   10                  15

Phe Tyr Pro Ile Glu Glu Gly Ser Ala Gly Ala Gln Leu Arg Lys Tyr
            20                  25                  30

Met Asp Arg Tyr Ala Lys Leu Gly Ala Ile Ala Phe Thr Asn Ala Leu
        35                  40                  45

Thr Gly Val Asp Tyr Thr Tyr Ala Glu Tyr Leu Glu Lys Ser Cys Cys
    50                  55                  60

Leu Gly Glu Ala Leu Lys Asn Tyr Gly Leu Val Val Asp Gly Arg Ile
65                  70                  75                  80
```

```
Ala Leu Cys Ser Glu Asn Cys Glu Glu Phe Ile Pro Val Leu Ala
                85                  90                  95

Gly Leu Phe Ile Gly Val Gly Val Ala Pro Thr Asn Glu Ile Tyr Thr
            100                 105                 110

Leu Arg Glu Leu Val His Ser Leu Gly Ile Ser Lys Pro Thr Ile Val
        115                 120                 125

Phe Ser Ser Lys Lys Gly Leu Asp Lys Val Ile Thr Val Gln Lys Thr
    130                 135                 140

Val Thr Ala Ile Lys Thr Ile Val Ile Leu Asp Ser Lys Val Asp Tyr
145                 150                 155                 160

Arg Gly Tyr Gln Ser Met Asp Asn Phe Ile Lys Lys Asn Thr Pro Gln
            165                 170                 175

Gly Phe Lys Gly Ser Ser Phe Lys Thr Val Glu Val Asn Arg Lys Glu
            180                 185                 190

Gln Val Ala Leu Ile Met Asn Ser Ser Gly Ser Thr Gly Leu Pro Lys
        195                 200                 205

Gly Val Gln Leu Thr His Glu Asn Ala Val Thr Arg Phe Ser His Ala
    210                 215                 220

Arg Asp Pro Ile Tyr Gly Asn Gln Val Ser Pro Gly Thr Ala Ile Leu
225                 230                 235                 240

Thr Val Val Pro Phe His His Gly Phe Gly Met Phe Thr Thr Leu Gly
            245                 250                 255

Tyr Leu Thr Cys Gly Phe Arg Ile Val Met Leu Thr Lys Phe Asp Glu
            260                 265                 270

Glu Thr Phe Leu Lys Thr Leu Gln Asp Tyr Lys Cys Ser Ser Val Ile
        275                 280                 285

Leu Val Pro Thr Leu Phe Ala Ile Leu Asn Arg Ser Glu Leu Leu Asp
    290                 295                 300

Lys Tyr Asp Leu Ser Asn Leu Val Glu Ile Ala Ser Gly Gly Ala Pro
305                 310                 315                 320

Leu Ser Lys Glu Ile Gly Glu Ala Val Ala Arg Arg Phe Asn Leu Pro
            325                 330                 335

Gly Val Arg Gln Gly Tyr Gly Leu Thr Glu Thr Thr Ser Ala Ile Ile
            340                 345                 350

Ile Thr Pro Glu Gly Asp Asp Lys Pro Gly Ala Ser Gly Lys Val Val
        355                 360                 365

Pro Leu Phe Lys Ala Lys Val Ile Asp Leu Asp Thr Lys Lys Thr Leu
    370                 375                 380

Gly Pro Asn Arg Arg Gly Glu Val Cys Val Lys Gly Pro Met Leu Met
385                 390                 395                 400

Lys Gly Tyr Val Asp Asn Pro Glu Ala Thr Arg Glu Ile Ile Asp Glu
            405                 410                 415

Glu Gly Trp Leu His Thr Gly Asp Ile Gly Tyr Tyr Asp Glu Glu Lys
            420                 425                 430

His Phe Phe Ile Val Asp Arg Leu Lys Ser Leu Ile Lys Tyr Lys Gly
        435                 440                 445

Tyr Gln Val Pro Pro Ala Glu Leu Glu Ser Val Leu Leu Gln His Pro
    450                 455                 460

Asn Ile Phe Asp Ala Gly Val Ala Gly Val Pro Asp Pro Ile Ala Gly
465                 470                 475                 480

Glu Leu Pro Gly Ala Val Val Val Leu Glu Lys Gly Lys Ser Met Thr
            485                 490                 495

Glu Lys Glu Val Met Asp Tyr Val Ala Ser Gln Val Ser Asn Ala Lys
```

```
                    500             505             510
Arg Leu Arg Gly Gly Val Arg Phe Val Asp Glu Val Pro Lys Gly Leu
        515                 520                 525

Thr Gly Lys Ile Asp Gly Lys Ala Ile Arg Glu Ile Leu Lys Lys Pro
    530                 535                 540

Val Ala Lys Met
545

<210> SEQ ID NO 2
<211> LENGTH: 30
<212> TYPE: DNA
<213> ORGANISM: Artificial
<220> FEATURE:
<223> OTHER INFORMATION: primer

<400> SEQUENCE: 2
ggaattccat atggaaaaca tggagaacga                                  30

<210> SEQ ID NO 3
<211> LENGTH: 28
<212> TYPE: DNA
<213> ORGANISM: artificial
<220> FEATURE:
<223> OTHER INFORMATION: primer

<400> SEQUENCE: 3
gcggatcctg gaaaacatgg agaacgat                                    28

<210> SEQ ID NO 4
<211> LENGTH: 27
<212> TYPE: DNA
<213> ORGANISM: Artificial
<220> FEATURE:
<223> OTHER INFORMATION: primer

<400> SEQUENCE: 4
cgctcgagct tacatcttag caactgg                                     27

<210> SEQ ID NO 5
<211> LENGTH: 24
<212> TYPE: DNA
<213> ORGANISM: Artificial
<220> FEATURE:
<223> OTHER INFORMATION: synthesized oligonucleotide

<400> SEQUENCE: 5
tatgcaccac caccaccacc acgg                                        24

<210> SEQ ID NO 6
<211> LENGTH: 26
<212> TYPE: DNA
<213> ORGANISM: Artificial
<220> FEATURE:
<223> OTHER INFORMATION: synthesized oligonucleotide

<400> SEQUENCE: 6
gatcccgtgg tggtggtggt ggtgca                                      26

<210> SEQ ID NO 7
<211> LENGTH: 25
<212> TYPE: DNA
<213> ORGANISM: Artificial
<220> FEATURE:
<223> OTHER INFORMATION: primer

<400> SEQUENCE: 7
```
cgtctgcaat tattatcaca ccgga                                          25

<210> SEQ ID NO 8
<211> LENGTH: 28
<212> TYPE: DNA
<213> ORGANISM: Artificial
<220> FEATURE:
<223> OTHER INFORMATION: primer

<400> SEQUENCE: 8
gtcaaggcta tggtgcaaca gaaacaac                                       28

<210> SEQ ID NO 9
<211> LENGTH: 28
<212> TYPE: DNA
<213> ORGANISM: Artificial
<220> FEATURE:
<223> OTHER INFORMATION: primer

<400> SEQUENCE: 9
gttgtttctg ttgcaccata gccttgac                                       28

<210> SEQ ID NO 10
<211> LENGTH: 25
<212> TYPE: DNA
<213> ORGANISM: Artificial
<220> FEATURE:
<223> OTHER INFORMATION: primer

<400> SEQUENCE: 10
tcgtttctgt tacaccatag ccttg                                          25

<210> SEQ ID NO 11
<211> LENGTH: 25
<212> TYPE: DNA
<213> ORGANISM: Artificial
<220> FEATURE:
<223> OTHER INFORMATION: primer

<400> SEQUENCE: 11
tcgtttctgt tataccatag ccttg                                          25

<210> SEQ ID NO 12
<211> LENGTH: 32
<212> TYPE: DNA
<213> ORGANISM: Artificial
<220> FEATURE:
<223> OTHER INFORMATION: primer

<400> SEQUENCE: 12
gcacacagga gatcttgggt attacgatga ag                                  32

<210> SEQ ID NO 13
<211> LENGTH: 29
<212> TYPE: DNA
<213> ORGANISM: Artificial
<220> FEATURE:
<223> OTHER INFORMATION: primer

<400> SEQUENCE: 13
catttcttta tcgtgggtcg tttgaagtc                                      29

<210> SEQ ID NO 14
<211> LENGTH: 29
<212> TYPE: DNA
<213> ORGANISM: Artificial

```
<220> FEATURE:
<223> OTHER INFORMATION: primer

<400> SEQUENCE: 14
ggtctcactg gtaaacgtga cggtaaagc                                    29

<210> SEQ ID NO 15
<211> LENGTH: 32
<212> TYPE: DNA
<213> ORGANISM: Artificial
<220> FEATURE:
<223> OTHER INFORMATION: primer

<400> SEQUENCE: 15
cttcatcgta atacccaaga tctcctgtgt gc                                32

<210> SEQ ID NO 16
<211> LENGTH: 29
<212> TYPE: DNA
<213> ORGANISM: Artificial
<220> FEATURE:
<223> OTHER INFORMATION: primer

<400> SEQUENCE: 16
gacttcaaac gacccacgat aaagaaatg                                    29

<210> SEQ ID NO 17
<211> LENGTH: 29
<212> TYPE: DNA
<213> ORGANISM: Artificial
<220> FEATURE:
<223> OTHER INFORMATION: primer

<400> SEQUENCE: 17
gctttaccgt cacgtttacc agtgagacc                                    29

<210> SEQ ID NO 18
<211> LENGTH: 33
<212> TYPE: DNA
<213> ORGANISM: Artificial
<220> FEATURE:
<223> OTHER INFORMATION: primer

<400> SEQUENCE: 18
tttatcgtgg atcgtgctaa gtctttaatc aaa                               33

<210> SEQ ID NO 19
<211> LENGTH: 33
<212> TYPE: DNA
<213> ORGANISM: Artificial
<220> FEATURE:
<223> OTHER INFORMATION: primer

<400> SEQUENCE: 19
tttgattaaa gacttagcac gatccacgat aaa                               33

<210> SEQ ID NO 20
<211> LENGTH: 30
<212> TYPE: DNA
<213> ORGANISM: Artificial
<220> FEATURE:
<223> OTHER INFORMATION: template

<400> SEQUENCE: 20
caagcttggc actggccgtc gttttacaac                                   30
```

-continued

```
<210> SEQ ID NO 21
<211> LENGTH: 15
<212> TYPE: DNA
<213> ORGANISM: Artificial
<220> FEATURE:
<223> OTHER INFORMATION: primer

<400> SEQUENCE: 21
gttgtaaaac gacgg                                                    15
```

The invention is:

1. A composition comprising a mutant luciferase having the amino acid sequence of SEQ ID NO: 1, wherein said amino acid sequence has one or more mutations selected from the group consisting of 344V, 344I, 344A, and 344A+425L+438G, further wherein said mutant luciferase has reactivity to dATP which is equal to or less than 1/400 reactivity to ATP.

2. A kit for analyzing nucleic acid comprising the composition according to claim 1.

3. The composition according to claim 1, wherein the luciferase is derived from Luciola lateralis.

* * * * *